United States Patent [19]

Goupil

[11] Patent Number: 4,970,230
[45] Date of Patent: Nov. 13, 1990

[54] DRUGS CONTAINING A PSORALENE DERIVATIVE

[76] Inventor: Jean-Jacques Goupil, 30, Avenue du Président Wilson, 94230 Cachan, France

[21] Appl. No.: 395,283

[22] Filed: Aug. 9, 1989

Related U.S. Application Data

[63] Continuation of Ser. No. 161,360, Feb. 22, 1988, abandoned, which is a continuation of Ser. No. 822,952, Jan. 27, 1986, abandoned, which is a continuation of Ser. No. 498,275, May 26, 1983, abandoned.

[51] Int. Cl.$^5$ .................... A61K 31/35; C07D 493/04
[52] U.S. Cl. ...................................... 514/455; 549/282
[58] Field of Search ......................... 514/455; 549/282

[56] References Cited

U.S. PATENT DOCUMENTS 4,429,138  1/1982  Goupil ................................ 549/282

FOREIGN PATENT DOCUMENTS 871424  2/1979  Belgium ............................... 514/455
2409751  7/1979  France .
2003470  3/1979  United Kingdom .

OTHER PUBLICATIONS

The Merck Index, 9th Ed., Merck & Co. Inc., Rahway, N.J., 1976, p. 433.

Primary Examiner—Richard L. Raymond
Attorney, Agent, or Firm—Darby & Darby

[57] ABSTRACT

This invention relates to improvements to drugs containing as an active substance the 5-methoxypsoralene of formula:

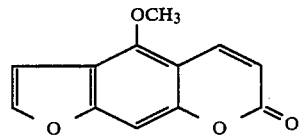

3 Claims, No Drawings

DRUGS CONTAINING A PSORALENE DERIVATIVE

This is a continuation of application Ser. No. 161,360, filed Feb. 22, 1988, now abandoned, which is a continuation of application Ser. No. 822,952, filed Jan. 27, 1986, now abandoned which is a continuation of application Ser. No. 498,275, filed May 26, 1983, now abandoned.

FIELD OF THE INVENTION

This invention relates to improvements to drugs containing as an active substance the 5-methoxypsoralene of formula:

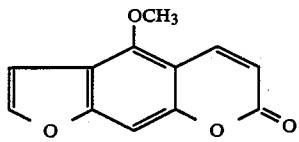

BACKGROUND OF THE INVENTION

French Pat. No. 77,31719 filed on Oct. 21, 1977 in the name of the present Applicant disclosed these new drugs as having a very high therapeutic index due to the very low toxicity of 5-methoxypsoralene compared to that of other psoralenes. The patent made clear that one could use therapeutic doses of 5-methoxypsoralene up to five times greater than those used for the 8-methoxypsoralene and advocated the administration of oral doses of 20 mg to 300 mg of 5-methoxypsoralene per day, followed by a daily exposure to A ultraviolets, at a rate of 1.5 to 10 joules/cm$^2$.

For topical administration, the patent advocated 5-methoxypsoralene concentrations between 100 ppm and 1000 ppm. The experimentations of the therapeutical activity of the new drugs had been carried out in the treatment of psoriasis, vitiligo, atypical eczema and mycosis fungoides.

It should be recalled here that the mycosis fungoides is a well known skin cancer of the lymphoma type, that is characterized by the proliferation of the lymphocyte cells more present in the lymph, that is the interstitial liquid irrigating notably the dermis and epidermis. The clinical experimentations which resulted in Pat. No. 77 31719 had been of course applied both on patients affected with psoriasis and patients affected with skin cancer, since one and the other of said illnesses are characterized by a more rapid than normal proliferation phenomenon of the cutaneous cells. Such a phenomenon of a too rapid proliferation of the cells is at the level of the deoxyribonucleic acid molecule present in the cell nucleus.

But it is known that the 5-methoxypsoralene, under the energetic action of a UV.A radiation gets fixed on each of the two helixes of the DNA molecule and therefore blocks any transmission of the message along said helixes, thereby stopping altogether the proteine synthesis and the cellular multiplication. In the normal cells, said blocking of the DNA helixes is cought up in speed by the DNA self-repair phenomena either by excision or by replication.

But in the case of cells affected with psoriasis or cancer, that is cells where the multiplication phenomena are very accelerated, the self-repair systems do not have time to set to work. In the same cells however the psoralene, by forming bridges between the two DNA helixes, stops the anarchical cellular multiplication. This explains that the 5-methoxypsoralene does not disturb in any way the multiplication of the normal cells and blocks selectively the diseased cells with accelerated proliferation which are the psoriatic cells and the cancerous cells.

THE INVENTION

After the satisfactory results obtained with the treatment of the mycosis fungoides lymphoma (cancer of the lymph cells) by administration of 5-methoxypsoralene and UV.A exposure, the Applicant had the idea of carrying on with investigations on other types of cancers or pre-cancerous lesions of the skin, that is proliferation tumors of the epidermic cells and no more the proliferation of the cells of the interstitial liquid such as the baso-cellular epithelioma, the spino-cellular epithelioma, the Hutchinson freckles, the actinic hyperkeratosis, the cutaneous melanomas, etc.

Such an idea was contrary to the well established general preconceived idea that the therapy associating the 5-methoxypsoralene and the UV.A radiation was totally inadvisable in the case of epidermal profileration tumors, since it was the solar radiation which was producing such tumors.

It is therefore quite unexpectedly that the Applicant found out that the 5-methoxypsoralene could heal epidermal proliferation cancerous tumors when administered under new and special conditions, notably as regards posology.

The pharmacological activity of the drug was brought to the fore by topical administration of 5-methoxypsoralene on mice having cancerous tumors produced by ultraviolets.

It appeared that the 5-methoxypsoralene necessary concentrations of the topical preparations used were very high: from 10 to 100 times more than the previously used concentrations, and this as a function of the excipient.

The general toxicity of the topical preparations having 1,000 to 10,000 ppm of 5-methoxypsoralene has been studied on the mouse with various excipients, and has shown that the active substance was well tolerated, even at such high doses. This corresponds to the fact the 5-methoxypsoralene is far less toxic than the 8-methoxypsoralene.

For this topical administration of 5-methoxypsoralene, various carriers have proved satisfactory. The hereafter examples are given by way of illustrations and are not limiting:
the pure petrolatums of various viscosities of the Codex,
the modified petrolatums as the salycilated petrolatum,
mineral oils,
vegetable oils, particularly the ethylenic oils comprising a small number of double bonds,
lanoline,
oily continuous phase emulsions,
alcoholic solutions, etc.

Due to the powerful barrier developped by the cancerous cells with regards to their environment, and notably the thickening phenomenon of the cellular membranes, the penetration of the drug by the topical route is slow and difficult.

According to the invention, it has been found that it was advantageous to introduce in the 5-methoxypsoralene topical preparation penetration agents such as:
the isopropyl myristate, the dimethyl sulphoxide (DMSO), etc.

The following clinical experimentations have been carried out with preparations containing 10,000 ppm pf 5-methoxypsoralene in pure petrolatum.

All volontary patients (a hundred about of them) had family antecedents and personal antecedents of a skin cancer. They all had had previously many ablations of skin cancers, and all the prior treatemnts had not checked the formation of recurrent cancers.

The types of cancers or pre-cancerous lesions of these patients which had been histologically proved were the following:
baso-cellular epitheliomas,
spino-cellular epitheliomas,
Hutchinson speckles,
actinic hyperkeratoses.

Some of these patients showed bilateral effects on the body or limbs allowing subjecting a lateral area to the treatment and keeping the other as a reference.

All the patients chosen had otherwise no serious illness.

All patients have been treated for five weeks in the following manner:

Twice a week, a pure petrolatum based preparation containing 10,000 ppm of 5-methoxypsoralene was applied on the tumor and on its sound close periphery (1 to 2 cm beyond the clinically evaluated limit of the tumor). From one to three hours after this application, the patient was subjected to an UV.A exposure with an energy of 5 joules/cm$^2$ to 10 joules/cm$^2$ (at the end of the treatment) after having reapplied the product a quarter of an hour prior to the exposure. The irradiation was applied to the whole area on which had been applied the 5-methoxypsoralene preparation.

The results were the following: the biopsies carried out at the end of the treatment, that is from the sixth week and later, showed a total necrosis of the tumor cancerous cells (as well as a healing up of the normal tissues).

New biopsies were carried out every six months following the treatment and showed no sign of recurrent or residual illness over a period of three years.

The tolerance to the drug and irradiation was perfect, that is without major phototoxic incident causing a prolongated stop of the treatment. Localized actinic erythemas, rapidly regressive, appeared on some patients who had a higher sensibility due mainly to their type of skin.

It should be remarked in this respect that the patients thus treated with total success had generally types of skin of the so-called type I, that is particularly liable to the skin cancers and notably to phototoxic incidents.

In other clinical experimentations on the same types of epidermic proliferation tumors, the treatment consisted in a topical administration of the 5-methoxypsoralene with concentrations of 1,000 to 10,000 ppm, doubled by an oral administration of tablets containing 5-methoxypsoralene and a UV.A exposure with an average energy of 5 joules/cm$^2$. There again the results were spectacular and showed the total necrosis of the cancerous cells.

The daily posology for the oral treatment of the cancerous tumors can reach 400 to 800 mg of 5-methoxypsoralene due to the low toxicity of the latter. It is always preferable to increase the dosis of active substance rather than the quantity of energy distributed so that the UV.A exposure should remain always within the range of 10 joules/cm$^2$.

In the case of cancerous tumors on the mucous membranes accessible by the natural routes, the treatment such as hereabove described is directly applicable, being understood that the UV.A radiation is penetrating to the very depth of the dermis. In the case of inner cancerous tumors, the administration of 5-methoxypsoralene has to be followed by an exposure to a more penetrating radiation with appropriate wave-lengths in order to bring the necessary energy to the deep sites.

I claim:

1. A method for the treatment of skin conditions selected from the group consisting of carcinomas of the epidermic cells, Hutchinson freckles, actinic hyperkeratoses and combinations thereof comprising:
applying topically on the affected skin of a patent in need of such treatment from 1,000–10,000 ppm of 5-methoxypsoralene in a pharmaceutically acceptable carrier; after said application, subjecting the treated area to ultraviolet A radiation having an energy of 5 jules/cm$^2$–10 joules/cm$^2$.

2. A method for the treatment of skin conditions selected from the group consisting of carcinomas of the epidermic cells, Hutchinson freckles, actinic hyperkeratoses, and combinations thereof, said method comprising:
administering to patients in need of such care by oral route 400–800 mg of 5-methoxpsoralene in a therapeutically acceptable carrier daily;
subjecting the affected skin area to ultravoilet A radiation having a energy of 5–10 joules/cm$^2$.

3. A method for the treatment of melanoma comprising:
applying topically on the affected skin of a patient in need of such treatment an amount of 5-methoxypsoralene ranging from in excess of 1000 and up to 10,000 ppm in a pharmaceutically acceptable carrier;
after said application, subjecting the treated skin to ultraviolet A radiation having an energy within the range of 5–10 joules/cm$^2$.

* * * * *